(12) United States Patent
Lim et al.

(10) Patent No.: US 8,377,071 B2
(45) Date of Patent: *Feb. 19, 2013

(54) SPACER WITH HEIGHT AND ANGLE ADJUSTMENTS FOR SPACING VERTEBRAL MEMBERS

(75) Inventors: Roy Lim, Germantown, TN (US); Kevin Foley, Germantown, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/214,822

(22) Filed: Aug. 22, 2011

(65) Prior Publication Data

US 2011/0307066 A1    Dec. 15, 2011

Related U.S. Application Data

(63) Continuation of application No. 12/816,476, filed on Jun. 16, 2010, now Pat. No. 8,025,665, which is a continuation of application No. 10/779,048, filed on Feb. 13, 2004, now Pat. No. 7,763,028.

(51) Int. Cl.
*A61B 17/58* (2006.01)
*A61B 17/68* (2006.01)
*A61B 17/66* (2006.01)
*A61F 2/44* (2006.01)

(52) U.S. Cl. ......... 606/90; 606/99; 606/105; 623/17.15; 623/17.16

(58) Field of Classification Search ............... 606/86 A, 606/86 B, 90, 99, 105; 623/17.11–17.16
See application file for complete search history.

(56) References Cited

U.S. PATENT DOCUMENTS 6,224,604 B1 * 5/2001 Suddaby .................... 606/80
6,605,105 B1 * 8/2003 Cuschieri et al. ........... 606/208

* cited by examiner

*Primary Examiner* — Eduardo C Robert
*Assistant Examiner* — Julianna N Harvey

(57) ABSTRACT

A device to space vertebral members that may include a deploying device with a first member with an elongated first shaft and a first body at an end of the first shaft, a second member with an elongated second shaft that extends around the first shaft and a second body at an end of the second shaft, and a third member with an elongated third shaft that extends around the second shaft and a third body at an end of the second shaft. The device may include a first plate positioned on a first side of the deploying device, and a second plate positioned on a second side of the deploying device. First, second, and third jointed linkages may be spaced apart along the deploying device and each having a pair of links and each having a first end attached to the first plate, a second end attached to the second plate, and an intermediate joint connecting the pair of links together and being attached to the deploying device.

20 Claims, 7 Drawing Sheets

SPACER WITH HEIGHT AND ANGLE ADJUSTMENTS FOR SPACING VERTEBRAL MEMBERS

REFERENCE TO RELATED APPLICATIONS

This application is a continuation of pending U.S. patent application Ser. No. 12/816,476, filed Jun. 16, 2010, which itself is a continuation of U.S. patent application Ser. No. 10/779,048, filed Feb. 13, 2004, and issued as U.S. Pat. No. 7,763,028. Each of these applications is herein incorporated by reference in its entirety.

BACKGROUND

Various devices are used for controlling the spacing between vertebral members. These devices may be used on a temporary basis, such as during surgery when it is necessary to access the specific surfaces of the vertebral members. One technique in which this type of device may be used is during preparing the endplates of a vertebral member. The devices may also remain permanently within the patient to space the vertebral members.

It is often difficult to position the device between the vertebral members in a minimally invasive manner. A device that is small may be inserted into the patient and between the vertebral members in a minimally invasive manner. However, the small size may not be adequate to effectively space the vertebral members. A larger device may be effective to space the vertebral members, but cannot be inserted into the patient and between the vertebral members in a minimally invasive manner.

The devices may also only allow for a minimum amount of adjustability. Once placed in the patient, the devices can only be altered to a small extent. Additionally, adjusting the devices may be difficult either from an ergonomic standpoint, or from the amount of force necessary for adjustment.

SUMMARY

The present invention is directed to a spacer to space vertebral members. The device may include a deploying device with an elongated first member including a first distal section with a nose and a first opening, an elongated second member with a second distal section with a first pair of arms that are spaced apart to receive the first distal section and being on opposing sides of the first distal section, and an elongated third member with a third distal section with a second pair of arms that are spaced apart to receive the second distal section with the second pair of arms being on opposing sides of the second distal section. The device may also include a first plate positioned on an upper side of the deploying device and a second plate positioned on a lower side of the deploying device. The device may include first, second, and third jointed linkages each having a pair of links and each having a first end attached to the first plate, a second end attached to the second plate, and an intermediate joint connecting the pair of links together and being attached to the deploying device. The intermediate joint of the first jointed linkage may be attached to the first member at a first opening, the intermediate joint of the second jointed linkage may be attached to the second member at a second opening, and the intermediate joint of the third jointed linkage may be attached to the third member at the third opening. The members may be nested together with the first distal section being axially movable relative to the second distal section between the first pair of arms to adjust a height measured between the first and second plates, and the second distal section being axially movable relative to the third distal section between the second pair of arms to adjust an angular orientation of the first and second plates.

The device may also include a deploying device with a first member with an elongated first shaft and a first body at an end of the first shaft, a second member with an elongated second shaft that extends around the first shaft and a second body at an end of the second shaft, and a third member with an elongated third shaft that extends around the second shaft and a third body at an end of the second shaft. The device may include a first plate positioned on a first side of the deploying device, and a second plate positioned on a second side of the deploying device. First, second, and third jointed linkages may be spaced apart along the deploying device and each having a pair of links and each having a first end attached to the first plate, a second end attached to the second plate, and an intermediate joint connecting the pair of links together and being attached to the deploying device. The intermediate joint of the first jointed linkage may be attached to the first body, the intermediate joint of the second jointed linkage may be attached to the first body and the second body, and the intermediate joint of the third jointed linkage may be attached to the third body. The first, second, and third members may be nested together with the first member axially movable relative to the second member to adjust a height measured between the first and second plates, and the second member axially movable relative to the third member to adjust an angular orientation of the first and second plates.

The device may include a first member with an elongated first shaft and a first connector at an end of the first shaft, a second member with an elongated second shaft that telescopingly receives the first shaft and a second connector at an end of the second shaft and is nested with the first connector, and a third member with an elongated third shaft that telescopingly receives the second shaft and a third connector at an end of the second shaft and is nested with the second connector. The device may include a first plate positioned on a first side of the deploying device, and a second plate positioned on a second side of the deploying device. A first jointed linkage may be attached to the first member, the first plate, and the second plate, a second jointed linkage may be attached to the second member, the first plate, and the second plate, with the second jointed linkage positioned inward towards the shafts from the first jointed linkage, and a third jointed linkage may be attached to the third member, the first plate, and the second plate, the third jointed linkage positioned inward towards the shafts from the second jointed linkage. The members may be axially movable relative to each other along a longitudinal axis to adjust the first and second plates.

DETAILED DESCRIPTION

Figure 7:
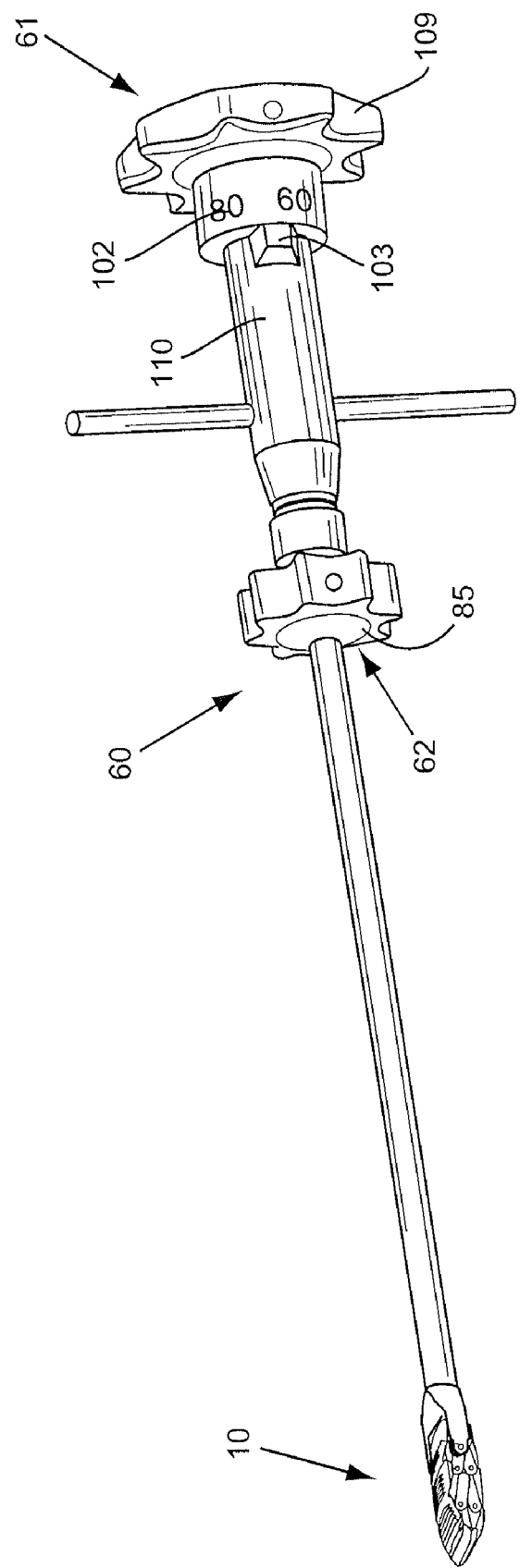
FIG. 7 is a perspective view of the spacer attached to the deploying device according to one embodiment of the present invention.

The present invention is directed to a tool to space vertebral members. The tool includes a spacer 10 and a deploying device 60 as illustrated in FIG. 7. The deploying device 60 controls both the height and the angle of the spacer 10. The spacer 10 is positioned on a distal end of the deploying device 60. The deploying device 60 has an elongated shape such that the spacer 10 is positioned between the vertebral members, and a proximal section of the mechanism is positioned a distance away to allow a physician to manipulate the height and angle.

Figure 2:
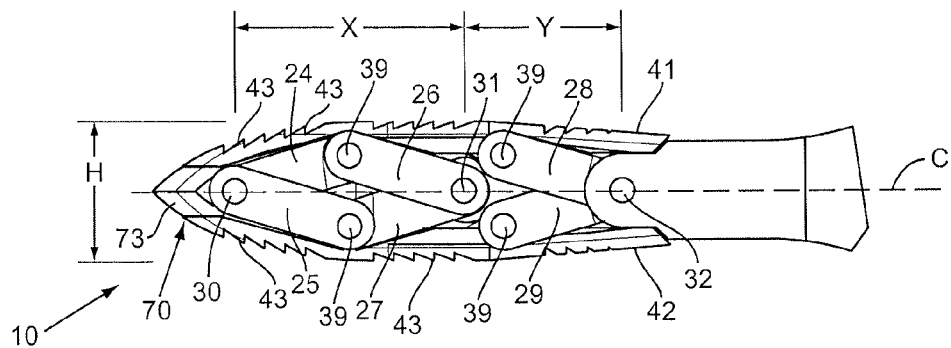
FIG. 2 is a side view illustrating the spacer in a closed orientation according to one embodiment of the present invention.
Figure 3:
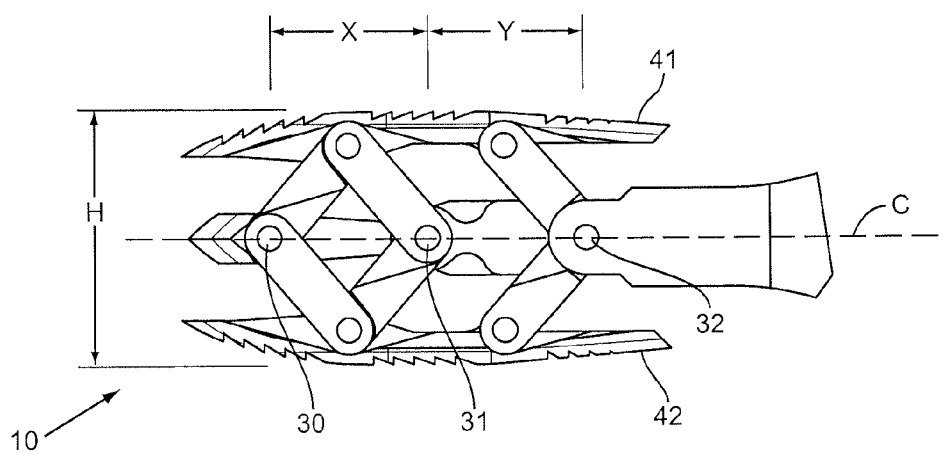
FIG. 3 is a side view illustrating the spacer in an open orientation according to one embodiment of the present invention.
Figure 4:
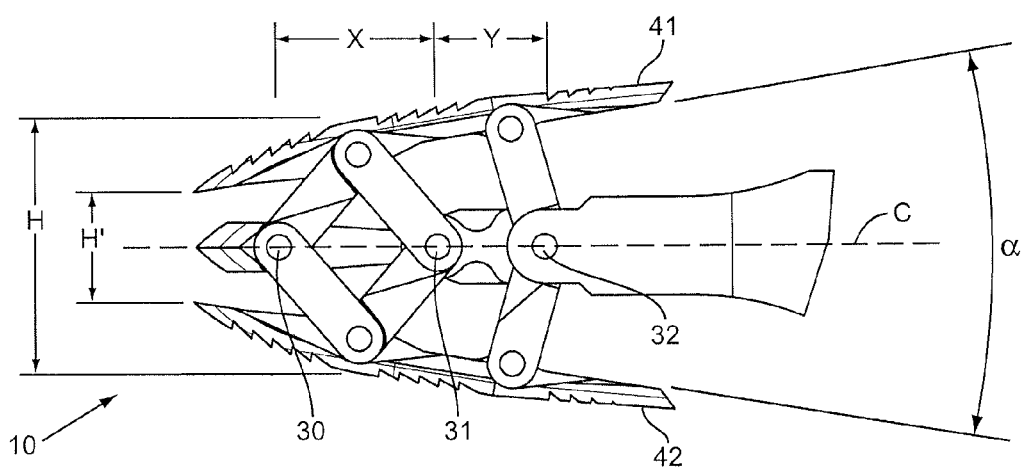
FIG. 4 is a side view illustrating the spacer in another open orientation according to one embodiment of the present invention.

The spacer 10 is selectively positionable between a closed orientation (FIG. 2) and an open orientation (FIGS. 3 and 4). The spacer 10 has an enlarged height in the open orientation defined by the distance between the upper and lower plates 41, 42. The plates 41, 42 move outward from a centerline C as the spacer 10 expands to the open position. The plates 41, 42 may also be angled relative to the centerline C to adjust for a variety of angles.

The first plate 41 and second plate 42 contact the vertebral members and form the outer surfaces of the spacer 10. As illustrated in embodiment of FIG. 2, each of the plates 41, 42 has an angled shape towards the distal end. A nose 73 at the distal end of the first member 70 of the deploying device 60 conforms to the angled shapes giving the device a bullet shape that facilitates insertion between the vertebral members. Ridges 43 may be positioned on the plates 41, 42 to secure the device 10 in the disc space between the vertebral members.

Figure 5:
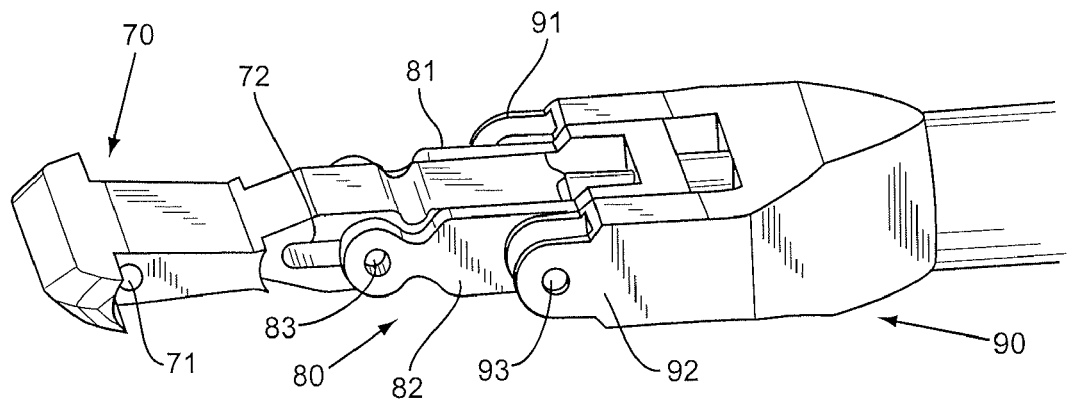
FIG. 5 is a perspective view of the distal end of the deploying device in a first orientation according to one embodiment of the present invention.
Figure 6:
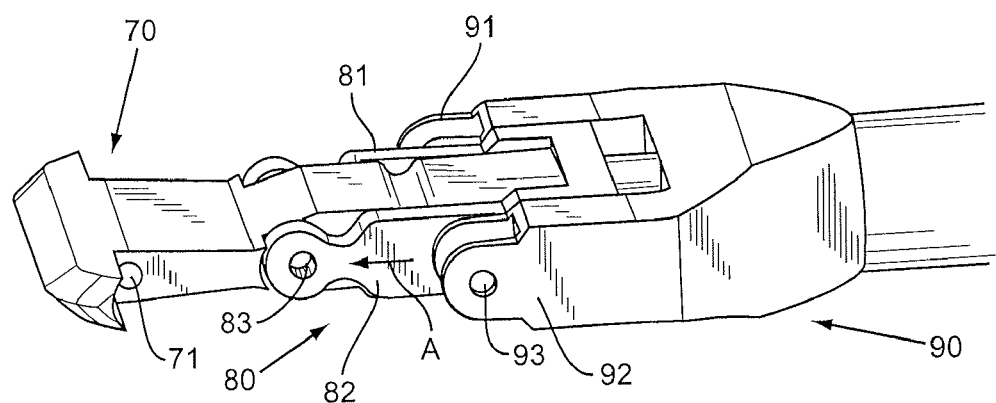
FIG. 6 is a perspective view of the distal end of the deploying device in a second orientation according to one embodiment of the present invention.

A deploying device 60 controls the positioning of the plates 41, 42. A distal end of the deploying device 60 is positioned within the plates 41, 42. As illustrated in FIGS. 5 and 6, the deploying device between the plates 41, 42 include a first member 70, a second member 80, and a third member 90. Relative movement of these members results in the deployment of the spacer 10 as will be explained in detail below. First member 70 includes a nose 73 having an angled configuration at the distal end. An aperture 71 and slot 72 are proximal to the nose. The distal end of the second member 80 includes a pair of arms 81, 82 that extend around the first member 70. Apertures 83 in each of the arms 81, 82 align with the slot 72 in the first member 70. The distal end of the third member 90 includes a first third member 91 and a second third member 92 that align on opposite sides of the second member 80. Apertures 93 are positioned towards the distal end of each third member 91, 92.

A series of links extend between the plates 41, 42 and the deploying device 60. The device includes links extending along both a first side and second side of the deploying device 60. Each side is substantially identical and only a first side will be explained in detail with the understanding that a corresponding link structure is also included on the second side. In one embodiment, each of the links has the same length.

Each of the links includes a first end attached to the deploying device 60, and a second end attached to one of the plates 41, 42. Specifically, the series of links include: link 24 extending between the first member 70 and the upper plate 41; link 25 extending between the first member 70 and the lower plate 42; link 26 extending between the second member 80 and the upper plate 41; link 27 extending between the second member 80 and the lower plate 42; link 28 extending between the third member 90 and the upper plate 41; and link 29 extending between the third member 90 and the lower plate 42.

Figure 1:
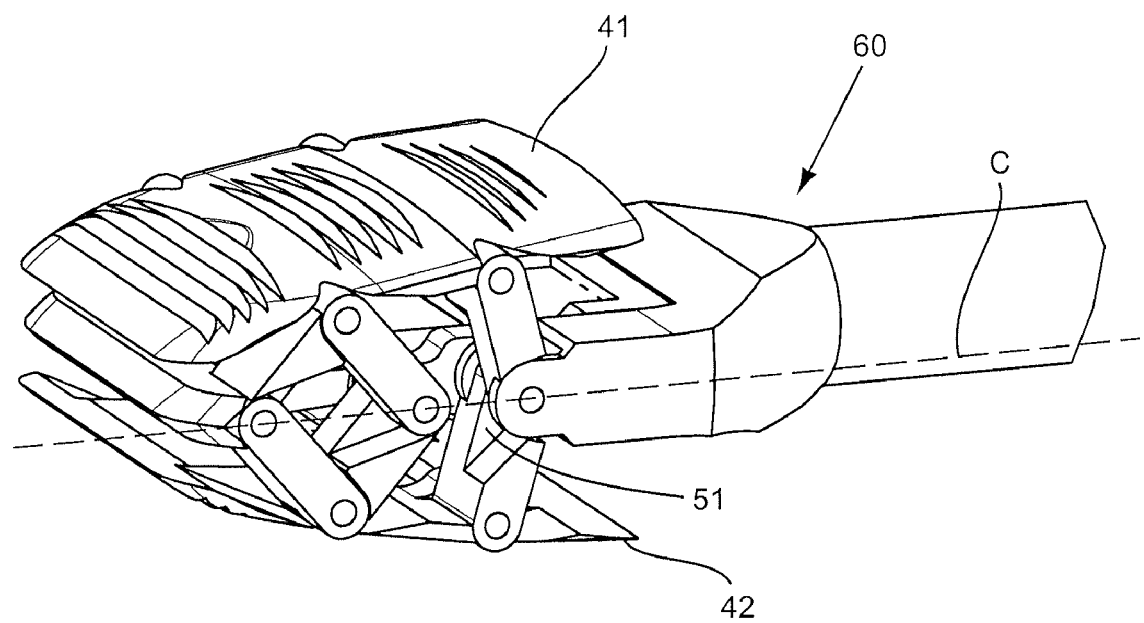
FIG. 1 is a perspective view of the spacer in an open orientation according to one embodiment of the present invention.

Each of the links is positioned in a two-pair combination that connects to the upper plate and the lower plate (i.e., link pair 24 and 25, link pair 26 and 27, link pair 28 and 29). The link pairs are constructed to overlap to conserve space and allow the plates 41, 42 to be positioned in closer proximity when the spacer 10 is in the closed orientation. In one embodiment as illustrated in FIG. 1, each link in the pair includes a complementary recessed shape 51. The recessed shapes 51 mate together in the closed orientation.

Links 24 and 26 and links 25 and 27 are operatively connected to form a linkage. Movement of one of the links of the linkage causes movement of the other link of the linkage. Embodiments of links, link pairs, and linkages are disclosed in U.S. patent application Ser. No. 10/178,960, filed Jun. 25, 2002, entitled "Minimally Invasive Expanding Spacer and Method", now U.S. Pat. No. 7,087,055, assigned to Warsaw Orthopedic, Inc., the owner of the current application, and herein incorporated by reference in its entirety.

Connection members pivotally connect the links to the plates 41, 42 and the deploying device 60. In one embodiment, a first connection member 30 extends through links 24, 25, through the aperture 71 in the first member 70, and through the corresponding links on the second side of the deploying device 60. Second connection member 31 extends through links 26, 27, apertures 83 in the second member 80, slot 72 in the first member 70, and through the corresponding links on the second side of the deploying device 60. Third connection member 32 extends through links 28, 29, and through aperture 93 in the third member 90. The third connection member 32 does not extend through the first member 70 or the second member 80. A corresponding connection member connects the two proximal links on the second side of the deploying device 60 10 to the third member 90. Additional connection members 39 connect the links to the plates 41, 42.

Deployment of the spacer 10 is caused by relative movement of members of the deploying device 60. FIG. 2 illustrates a side view of the spacer 10 in a closed orientation. In one embodiment, spacer 10 has a length of about 30 mm, a width of about 27 mm, and a height H of about 8.5 mm measured at the point of maximum convexity of the plates 41, 42. The first connection member 30 is distanced from the second connection member 31 a distance X. The second connection member 31 is distanced from the third connection member 32 a distance Y.

FIG. 3 illustrates the spacer 10 in an open orientation. The open orientation features the plates 41, 42 spaced from the centerline C. The expansion is caused by the first member 70 moving proximally relative to the second member 80 and the third member 90. The relative position of the first connection member 30 has moved relative to the second connection member 31 and the third connection member 32. This is seen as the distance X has decreased from that illustrated in FIG. 2. The distance Y between the second and third connection members 31, 32 remain the same. The force of the first member 70 moving proximally results in the links being deployed.

During the deployment, the first member 70 is proximally moved along the spacer 10. The movement results in the first connection member 30 that is positioned within aperture 71 also moving proximally. The second connection member 31 slides within the slot 72 in the first member 70 from a proximal end of the slot 72 when the spacer 10 is closed, to a distal end of the slot 72 when the spacer is deployed. This movement is illustrated in FIGS. 5 and 6 (second connection member 31 is removed in FIGS. 5 and 6 for clarity). The third connection member 32 is not connected to the first member 70 and therefore does not move. The deployment by moving the first member 70 results in the plates 41, 42 being substantially parallel during the range of deployment. The height of the spacer 10 is controlled by the amount of movement of the first member 70. In one embodiment, the height H of the spacer is about 15.4 mm measured from the points of maximum convexity of the plates 41, 42.

FIG. 4 illustrates the spacer 10 with the plates 41, 42 in the open orientation and at an angle relative to the centerline C. The angle α is the angle formed by both plates 41, 42. In one embodiment, angle α is referred to as the lordotic angle. In one embodiment, the angle α may range from about 0° to about 19°. The angle α is formed by moving the third connection member 32 relative to the second connection member 31. As illustrated in FIGS. 3 and 4, third member 90 is moved proximally causing the plates 41, 42 to form the angle α. The distance Y between the second and third connection members 31, 32 is decreased causing the proximal links 28, 29 to push outward on the proximal sections of the plates 41, 42. The relative movement between the second and third connection members 31, 32 controls the degree of the angle α. In one embodiment, the distance between the distal ends of the plates 41, 42 is about 6.7 mm.

FIGS. 5 and 6 illustrate the relative movement of the second and third members 80, 90 (third connection member 32 has been removed from FIGS. 5 and 6 for clarity). The third connection member 32 positioned within aperture 93 extends through the third member 90 without extending through the second member 80. Therefore, movement of the third member 90 does not result in movement of the second member 80. As the third member 90 moves in the direction of arrow A, the amount of angle α increases accordingly.

Figure 8:
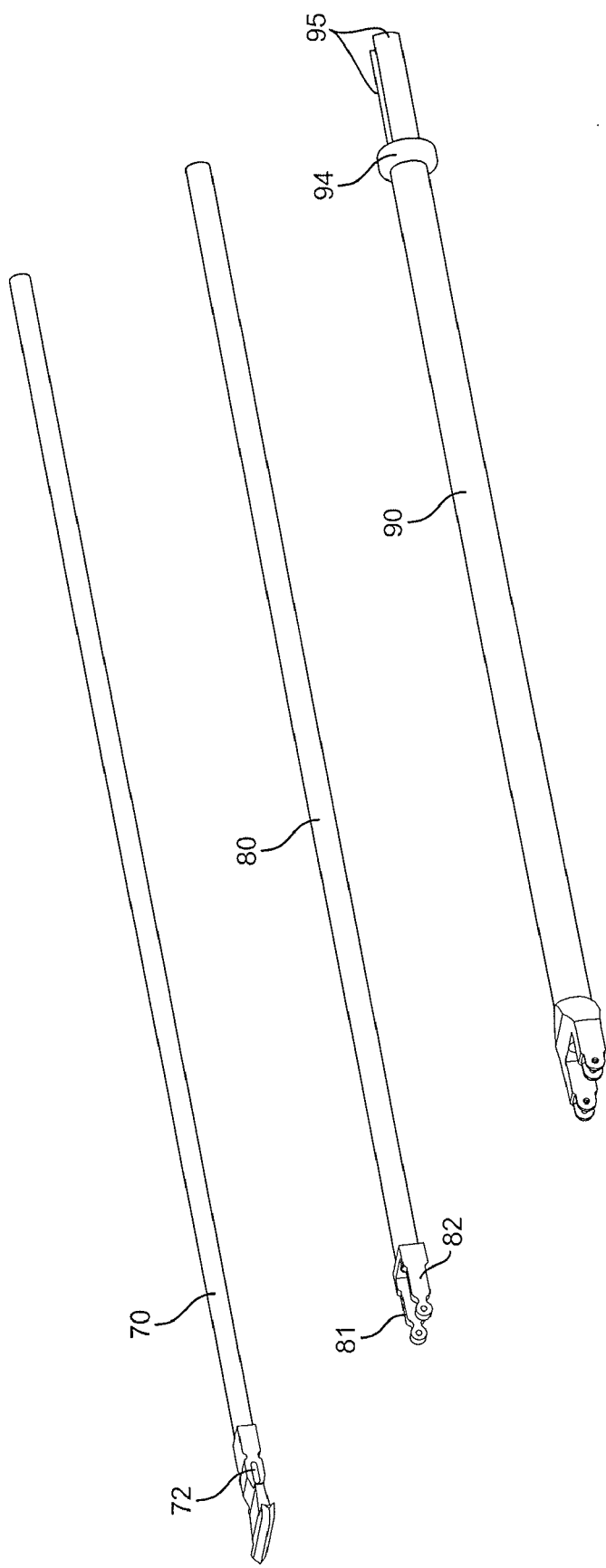
FIG. 8 is an exploded view of the first member, second member, and third member according to one embodiment of the present invention.

The deploying device 60 causes the spacer 10 to move between the open and closed orientations, and also between a variety of angles α. Deploying device 60 includes a first deploying device 61 for changing the height of the spacer 10, and a second deploying device 62 for changing the angle α. As illustrated in FIGS. 7 and 8, the proximal end of deploying device 60 is distanced from the distal end for the physician to remotely control the size and angle of the spacer 10. In one embodiment, the first member 70 includes an elongated proximal section that fits within an elongated section of the second member 80. The first member 70 is sized to move within the second member 80. The elongated section of the second member 80 with the internal proximal first member fits within the third member 90. The third member 90 is sized to move relative to the second member 80.

Figure 9:
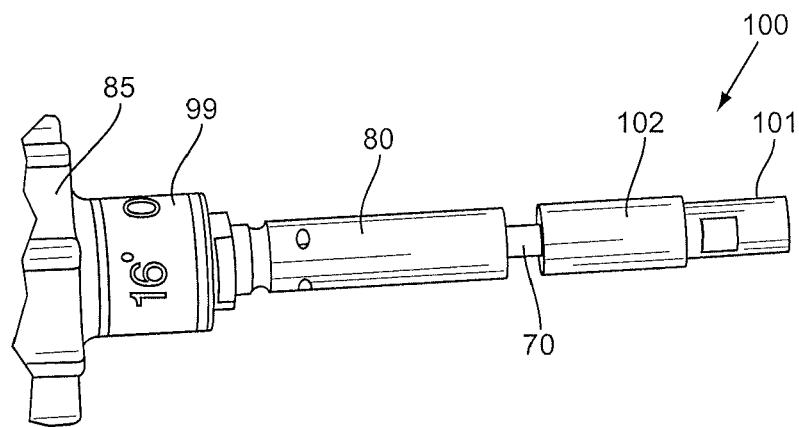
FIG. 9 is a partial side view of the proximal section of the first member and second member according to one embodiment of the present invention.

A first deploying device 61 for changing the height of the spacer 10 is illustrated in FIGS. 7 and 9. First member 70 includes a lock 100 mounted to the proximal end. Lock 100 includes a seat 101 and a sleeve 102 each having a larger cross-sectional size than a hollow interior of the second member 80. The first member 70 may be moved axially along the second member 80 between a point where the distal end of the sleeve 102 contacts the proximal end of the second member 80, and a distance where the distal sleeve end is spaced from the proximal second member end (as illustrated in FIG. 9). In one embodiment, an axial force applied to the first member 70 moves the first member relative to the second member 80. In another embodiment, the distal end of the first member 70 is threaded and mates with threads on the interior of the sleeve 102. Rotation of the sleeve 102 causes the sleeve to move along the first member 70 with the distal end of the sleeve 102 contacting and pushing the proximal end of the second member 80. Continued rotation causes the first member 70 to be pulled proximally relative to the second member 80. In both embodiments, the proximal movement of the first member 70 causes the height of the spacer 10 to increase. A force applied in the opposite direction, or rotation of the sleeve 102 in the opposite direction allows for the first member 70 to be moved distally relative to the second member 80 to reduce the height of the spacer 10.

In the rotational embodiment explained above, a knob 109 may be connected to the sleeve 102 as illustrated in FIG. 7. A gauge 102 may be positioned adjacent to the knob 101 to determine the height of the spacer 10. In one embodiment, gauge 102 includes a progressive scale that aligns with a reference point 103. The height of the spacer 10 can be determined by the position of the gauge 102 relative to the reference point 103.

Figure 10:
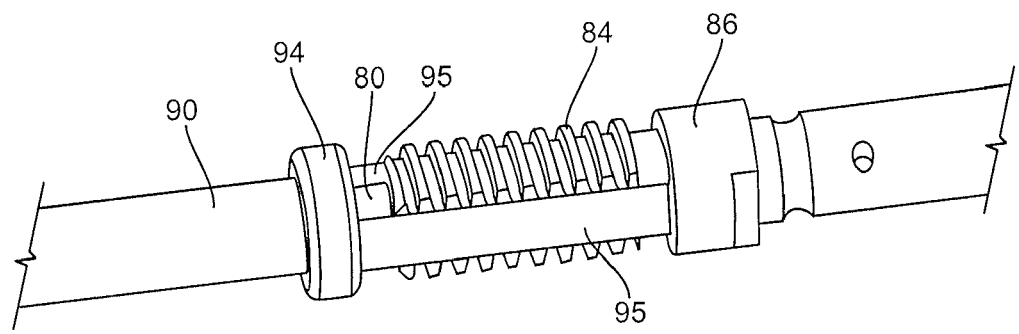
FIG. 10 is a partial side view of the proximal section of the second member and third member according to one embodiment of the present invention.

A second deploying device 62 controls the angle α. As illustrated in FIGS. 8 and 10, the proximal end of the third member 90 includes an extension 94 and a pair of spaced apart fingers 95. The proximal end of the second member 80 includes a threaded section 84 with a threaded knob 85 (FIG. 7). The knob 85 is rotated about the threaded section 84 with a distal end of the knob contacting the extension 94 to move the third member 90 in a distal direction and thus adjusting the amount of angle α. The amount of rotation of the knob 85 controls the amount of angle α. As illustrated in FIG. 9, a gauge 99 may be placed adjacent to the knob 85 to determine the amount of rotation and thus the amount of spacer angle α.

Figure 11:
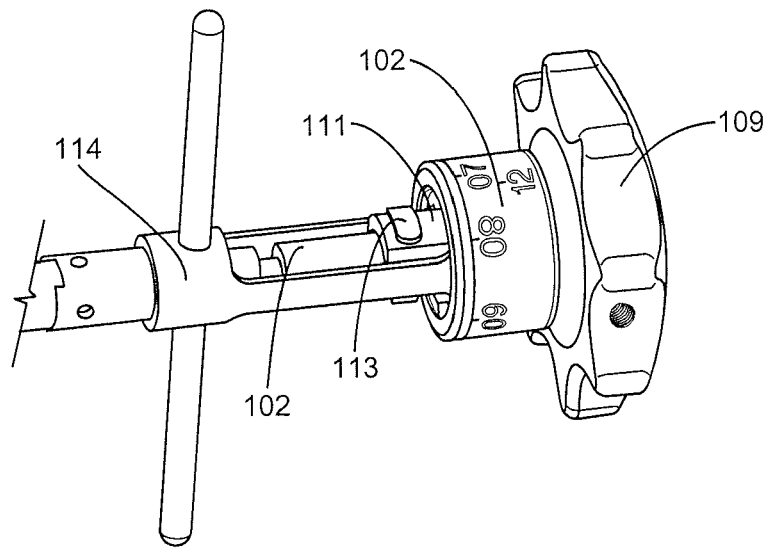
FIG. 11 is a partial perspective view of the first deploying device according to one embodiment of the present invention.
Figure 12:
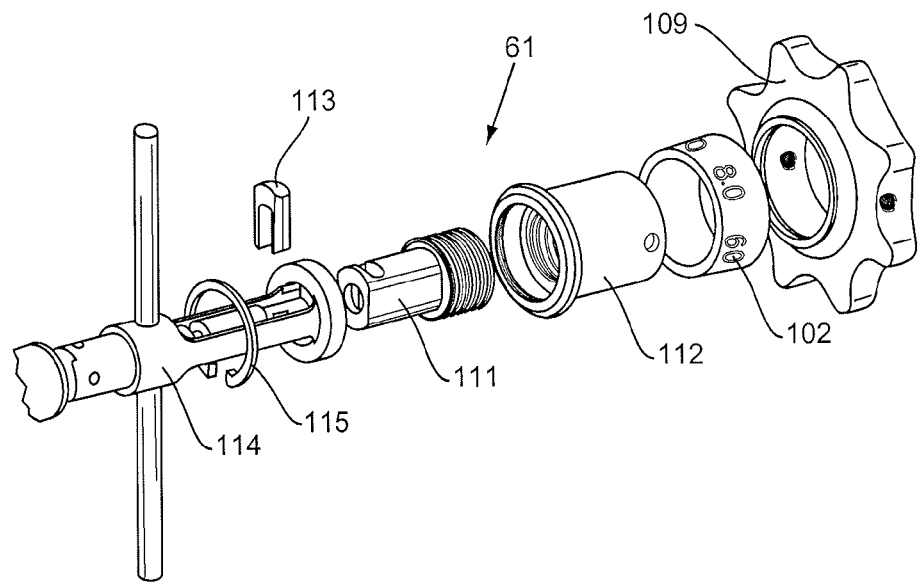
FIG. 12 is an exploded view of the first deploying device according to one embodiment of the present invention.

FIG. 7 illustrates a cover 110 extending over the proximal section of the deploying device 60. FIG. 11 illustrates the proximal section without the cover 110. FIG. 12 illustrates an exploded view of the proximal section of the first deploying device 61 that controls the spacer height. A screw 111 is connected to the seat 101 and a frame 114 is connected to the second member 80. A sleeve 112 is mated to the frame 114 and is retained by a retaining ring 115. The retaining ring 115 rotates freely about the third member 90 (not illustrated). Rotation of the knob 109 rotates the sleeve 112 and moves the screw 111 proximally. This proximal movement provides the distraction of the spacer 10. Lock 113 is inserted into an aperture in screw 111 and mates with machined flats on seat 101.

Figure 13:
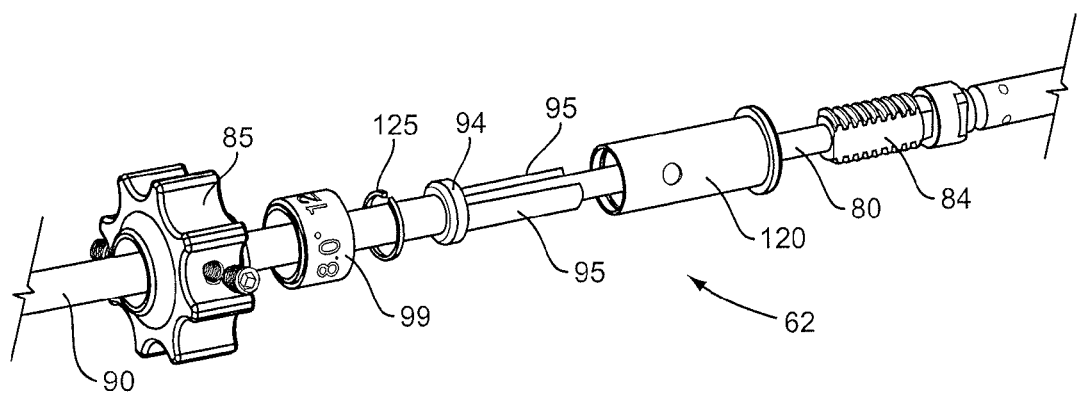
FIG. 13 is an exploded view of the second deploying device according to one embodiment of the present invention.

FIG. 13 illustrates an exploded view of the second deploying device 62. The distal end of the third member 90 includes spaced apart forks 95. The second member 80 is positioned within the third member and the threaded section 84 is positioned at a proximal end of the forks 95. A sleeve 120 extends over the fork 95 and is retained by a retaining ring 125. The retaining ring rotates freely about the third member 90. An internal thread on the sleeve 120 engages with the threaded section 84 on the second member 80. The forks 95 are machined to index with machined edges of the threaded section 84. Rotation of the knob 85 rotates the sleeve 120 that travels along the thread of the threaded section 84 and moves the third member 90 to move distally.

The arrangement of the first member 70, second member 80, and third member 90 may have a variety of configurations. In the embodiments illustrated, the first member 70 and second member 80 are nested within the third member 90. In other embodiments, the first member 70 and/or second member 80 may be positioned external to each other and the third member 90. The various arrangements should provide for relative movement of the members of the deploying device 60 to allow for changes in height and angles.

The angle α of the spacer 10 may also be negative with the proximal ends of the plates 41, 42 being in closer proximity than the distal ends. This is accomplished by moving the third connection member 32 proximally relative to the second connection member 31.

The term vertebral member is used generally to describe the vertebral geometry comprising the vertebral body, pedicles, lamina, and processes. The spacer 10 may be sized and shaped, and have adequate strength requirements to be used within the different regions of the vertebra including the cervical, thoracic, and lumbar regions. In one embodiment, spacer 10 is positioned within the disc space between adjacent vertebrae. Plates 50 contact the end plates of the vertebra to space the vertebra as necessary. In one embodiment, the spacer 10 is inserted posteriorly in the patient. In another embodiment, the spacer 10 is inserted anteriorly into the patient. In another embodiment, the spacer is inserted laterally into the patient.

In another embodiment (not illustrated), spacer 10 includes only one moving plate. A first plate moves as discussed above, and a second plate is stationary. The links move outward from the stationary plate to expand the height of the spacer 10 to the open orientation. This embodiment may include any number of links depending upon the desired spacing and strength requirements. In one embodiment, the first plate 41 expands away from the plate 42 by links 24, 26, 28.

The spacer 10 may be removable from the deploying device 60. The spacer 10 may be temporarily left between the vertebral members with the deployment mechanism removed during the procedure to provide the physician with a better view and greater work area. After the procedure, the spacer 10 may remain within the patient between the vertebral members, or the deploying device 60 may be re-engaged for spacer removal. The spacer 10 may also be returned to the closed orientation after re-engagement and prior to the spacer 10 being removed from the patient.

The present invention may be carried out in other specific ways than those herein set forth without departing from the scope and essential characteristics of the invention. In one embodiment, spacer 10 and delivery device 80 are constructed of stainless steel. In one embodiment, the distal ends of the plates 41, 42 contact in the closed orientation. The first deploying device 61 may be positioned proximal to or distal to the second deploying device 62. The present embodiments are, therefore, to be considered in all respects as illustrative and not restrictive, and all changes coming within the meaning and equivalency range of the appended claims are intended to be embraced therein.

What is claimed is:

1. A device to space vertebral members comprising:
    a deploying device comprising:
        an elongated first member including a first distal section with a nose and a first opening;
        an elongated second member with a second distal section with a first pair of arms that are spaced apart to receive the first distal section and being on opposing sides of the first distal section, the second distal section including a second opening that is parallel to the first opening;
        an elongated third member with a third distal section with a second pair of arms that are spaced apart to receive the second distal section with the second pair of arms being on opposing sides of the second distal section, the third distal section including a third opening;
    a first plate comprising a first surface and a second surface, the first surface engaging an upper side of the deploying device, the second surface comprising a plurality of planar angled ridges extending parallel to one another configured to engage tissue;
    a second plate comprising a first surface and a second surface, the first surface of the second plate engaging a lower side of the deploying device, the second surface of the second plate comprising a plurality of planar angled ridges extending parallel to one another;
    first, second, and third jointed linkages each comprising a pair of links and each having a first end attached to the first plate, a second end attached to the second plate, and an intermediate joint connecting the pair of links together and being attached to the deploying device, the intermediate joint of the first jointed linkage being attached to the first member at the first opening, the intermediate joint of the second jointed linkage being attached to the second member at the second opening, and the intermediate joint of the third jointed linkage being attached to the third member at the third opening;
    the first, second, and third members being nested together with the first distal section being axially movable relative to the second distal section between the first pair of arms to adjust a height measured between the first and second plates, and the second distal section being axially movable relative to the third distal section between the second pair of arms to adjust an angular orientation of the first and second plates.

2. The device of claim 1, wherein the first member includes an elongated first shaft that extends outward from the first distal section and the second member includes an elongated second shaft that extends outward from the second distal section, the first shaft telescopes within an interior of the second shaft.

3. The device of claim 2, wherein the third member includes an elongated third shaft with an interior that telescopingly receives the first and second shafts.

4. The device of claim 1, wherein the intermediate joints of the first and second jointed linkages are spaced apart along the first and second plates for the plates to remains relatively parallel to a longitudinal axis of the deploying device during axial movement of the first member relative to the second member.

5. The device of claim 1, wherein each of the first and second plates contact the nose of the first distal section when the plates are in closed orientation.

6. The device of claim 1, wherein the first and second jointed linkages are both connected to the first plate at a first common point and to the second plate at a second common point.

7. The device of claim 1, wherein a connection member extends through the intermediate joint of the second linkage and the second opening of the second member, and a connection member extends through the intermediate joint of the first linkage and the first opening of the first member.

8. The device of claim 1, wherein the first, second, and third members are each aligned in a collinear arrangement.

9. A device to space vertebral members comprising:
   a deploying device comprising:
     a first member with an elongated first shaft and a first body at an end of the first shaft;
     a second member with an elongated second shaft that extends around the first shaft and a second body at an end of the second shaft;
     a third member with an elongated third shaft that extends around the second shaft and a third body at an end of the second shaft;
   a first plate comprising a first surface and a second surface, the first surface engaging a first side of the deploying device, the second surface comprising a plurality of planar ridges extending parallel to one another configured to engage tissue;
   a second plate comprising a first surface and a second surface, the first surface of the second plate engaging a second side of the deploying device, the second surface of the second plate comprising a plurality of planar angled ridges extending parallel to one another configured to engage tissue;
   first, second, and third jointed linkages spaced apart along the deploying device and each comprising a pair of links and each having a first end attached to the first plate, a second end attached to the second plate, and an intermediate joint connecting the pair of links together and being attached to the deploying device, the intermediate joint of the first jointed linkage being attached to the first body, the intermediate joint of the second jointed linkage being attached to the first body and the second body, and the intermediate joint of the third jointed linkage being attached to the third body;
   the first, second, and third members being nested together with the first member axially movable relative to the second member to adjust a height measured between the first and second plates, and the second member axially movable relative to the third member to adjust an angular orientation of the first and second plates.

10. The device of claim 9, wherein the first, second, and third jointed linkages are attached to a first lateral side of the deploying device, and fourth, fifth, and sixth jointed linkages are attached to a second lateral side of the deploying device.

11. The device of claim 9, wherein the first body includes a tapered nose that faces away from the first shaft.

12. The device of claim 9, wherein the first body includes an elongated slot that extends along a longitudinal axis of the deploying device and the second body includes an aperture that aligns with the slot, the slot including a greater length measured along the longitudinal axis of the deploying device than the aperture.

13. The device of claim 12, further comprising a connection member that extends through the elongated slot, the aperture, and the intermediate joint of the second jointed linkage.

14. The device of claim 9, wherein the first ends of the first and second jointed linkages attaches to a first point along the first plate, and the first end of the third jointed linkage attaches to a second point along the first plate that is spaced apart from the first point.

15. The device of claim 9, wherein the second body includes a first pair of arms that are spaced apart to receive the first body, and the third body includes a second pair of arms that are spaced apart to receive the second body.

16. The device of claim 9, wherein each of the first, second, and third shafts are straight and are collinear.

17. A device to space vertebral members comprising:
   a first member with an elongated first shaft and a first connector at an end of the first shaft;
   a second member with an elongated second shaft that telescopingly receives the first shaft and a second connector at an end of the second shaft, the second connector being nested with the first connector;
   a third member with an elongated third shaft that telescopingly receives the second shaft and a third connector at an end of the second shaft, the third connector being nested with the second connector;
   a first plate comprising a first surface and a second surface, the first surface engaging a first side of the deploying device, the second surface comprising a plurality of planar angled ridges extending parallel to one another configured to engage tissue;
   a second plate comprising a first surface and a second surface, the first surface engaging a second side of the deploying device, the second surface of the second plate comprising a plurality of planar angled ridges extending parallel to one another configured to engage tissue;
   a first jointed linkage attached to the first member, the first plate, and the second plate;
   a second jointed linkage attached to the second member, the first plate, and the second plate, the second jointed linkage positioned inward towards the shafts from the first jointed linkage;
   a third jointed linkage attached to the third member, the first plate, and the second plate, the third jointed linkage positioned inward towards the shafts from the second jointed linkage;
   the members being axially movable relative to each other along a longitudinal axis to adjust the first and second plates.

18. The device of claim 17, wherein each of the shafts is straight and collinear.

19. The device of claim 17, wherein the first and second jointed linkages are attached to the first plate at a common point.

20. The device of claim 17, wherein the first and second members are axially movable to adjust a distance between intermediate joints of the first and second jointed linkages to adjust a distance between the plates.

* * * * *